United States Patent [19]

Klaenhammer et al.

[11] Patent Number: 5,580,725
[45] Date of Patent: Dec. 3, 1996

[54] METHOD OF ELIMINATING GENETIC ROUTES FOR BACTERIOPHAGE EVOLUTION AND PRODUCTS PRODUCED THEREBY

[75] Inventors: Todd R. Klaenhammer, Raleigh, N.C.; Sylvain Moineau, Bradenton, Fla.

[73] Assignee: North Carolina State Universtiy, Raleigh, N.C.

[21] Appl. No.: 229,548

[22] Filed: Apr. 19, 1994

[51] Int. Cl.$^6$ .............................. C12N 15/63; C12Q 1/68; C12Q 1/70

[52] U.S. Cl. ................................ 435/6; 435/5; 435/172.3; 435/235.1; 435/252.3; 435/252.9; 935/55; 935/72

[58] Field of Search ...................... 435/6, 5, 235.1, 435/252.3, 252.9, 172.3; 935/55, 72

[56] References Cited

U.S. PATENT DOCUMENTS

| | | | |
|---|---|---|---|
| 4,530,904 | 7/1985 | Hershberger et al. | 435/172.3 |
| 4,883,756 | 11/1989 | Klaenhammer et al. | 435/252.3 |
| 4,931,396 | 6/1990 | Klaenhammer et al. | 435/252.3 |
| 5,139,950 | 8/1992 | Klaenhammer et al. | |

FOREIGN PATENT DOCUMENTS

| | | |
|---|---|---|
| 0183469A1 | 6/1986 | European Pat. Off. . |
| 0474464A2 | 3/1992 | European Pat. Off. . |

OTHER PUBLICATIONS

Durmaz et al. J. Bacteriology 174(22):7463–7469, 1992.
Sanders et al. Applied and Evironmental Microbiology 52(5):1001–1007, 1986.
Fitzgerald et al. J. Chem. Tech. and Biotech. 58:195–199, 1993.

O'Sullivan et al., *Effect of Increasing the Copy Number of Bacteriophage Origins of Replication, in Trans, on Incoming–Phage Proliferation*, Applied and Environmental Microbiology, vol. 59, No. 8, Aug. 1993, pp. 2449–2456.

Alatossava et al., *Molecular Characterization of Three Small Isometric–Headed Bacteriophages Which Vary in Their Sensitivity to the Lactococcal Phage Resistance Plasmid pTR2030*, Applied and Environmental Microbiology, vol. 57, No. 5, May 1991, pp. 1346–1353.

Todd R. Klaenhammer, *Development of Bacteriophage–Resistant Strains of Lactic Acid Bacteria*, Biochem. Soc. Trans., vol. 19, No. 3, Aug. 1991, pp. 675–681.

PCT International Search Report. (PCT/US95/04429).

R.K. Thunell et al., *Phage–Insensitive, Multiple–Strain Approach to Cheddar Cheese Making$^a$*, J. Dairy Science 64, pp. 2270–2277. (1981).

T.R. Klaenhammer, *Genetic Characterization of Multiple Mechanisms of Phage Defense from a Prototype Phage–Insensitive Strain, Lactococcus Iactis ME2[1]*, J. Dairy Science 72, pp. 3429–3443 (1989).

Colin Hill, *Bacteriophage and bacteriophage resistance in lactic acid bacteria*, FEMS Microbiology Reviews 12 pp. 87–108 (1993).

*Primary Examiner*—Stephanie W. Zitomer
*Assistant Examiner*—Paul B. Tran
*Attorney, Agent, or Firm*—Bell, Seltzer, Park & Gibson

[57] ABSTRACT

A process of identifying and disrupting bacterial DNA sequences that contribute to the evolution of new lytic bacteriophages is described. Vectors and recombinant bacteria for use in producing fermentative starter cultures and culture media resistant to the appearance of new phages, and methods of producing such vectors and recombinant bacteria, are described.

6 Claims, 3 Drawing Sheets

5,580,725

METHOD OF ELIMINATING GENETIC ROUTES FOR BACTERIOPHAGE EVOLUTION AND PRODUCTS PRODUCED THEREBY

FIELD OF THE INVENTION

The present invention relates to a process of identifying and disrupting bacterial DNA sequences that contribute to the evolution of new lytic bacteriophages. The present invention also relates to vectors and bacteria used in and produced by the present methods.

BACKGROUND OF THE INVENTION

Production of cheese and cultured dairy products have long relied on the fermentation of milk with lactococci (previously classified as the group N Streptococci), such as *Lactococcus lactis* subsp. *lactis, Lactococcus lactis* subsp. *cremoris*, and *Lactococcus lactis* subsp. *lactis* biovar. *diacetylactis* (also called *Lactococcus diacetylactis*). These bacteria are responsible for the acid development, flavor production, and often coagulum characteristics in mesophilic dairy fermentations. Because efficient milk fermentations are dependent on the growth and activity of the lactococci, care is exercised to prepare bacterial starter cultures that are highly active and uncontaminated with undesirable microorganisms or bacteriophages. However, the fermentation process itself is nonaseptic, occurring in open vats with a nonsterile medium (pasteurized milk). For the majority of strains of lactococci employed in commercial dairy fermentations, lytic bacteriophages capable of halting growth and acid production can appear within one to two days after introducing the starter culture into the cheese plant. Bacteriophage contamination of numerous industrial fermentations other than milk fermentations have also been observed. Lytic phages continue to disrupt fermentative activities and cause substantial economic losses, most notably in the cultured dairy product industries (See, e.g., T. Klaenhammer, *Biochemical Society Transactions,* 19:675(1991)).

The increased production capacity and process efficiency in the dairy industry in recent decades has necessitated the use of defined mixtures of lactococci capable of uniform and rapid rates of acid production. With the selection of highly fermentative lactococci and their propagation under aseptic conditions (in the absence of bacteriophages), the majority of cultures now used by the industry are highly susceptible to bacteriophage attack upon introduction into the factory environment. A number of methods have been developed to minimize phage action during commercial milk fermentations, including the use of concentrated cultures, aseptic bulk starter vessels and phage-inhibitory media (see, e.g., U.S. Pat. No. 4,282,255). However, phage contamination cannot be prevented following entrance into the fermentation vat. Emphasis for protection of the culture therefore has shifted to minimizing prolific phage-host interactions through rotation of phage-unrelated strains or the use of phage-resistant mutants in multiple-strain starters. Although in theory strain rotation should minimize developing phage populations within the plant, in practice it has been shown that rotations of large numbers of strains can lead to an increase in phage populations and diversity within a cheese plant (See R. Thunell et al., *J. Dairy Sci.* 64, 2270–2277 (1981)).

Hershberger, U.S. Pat. No. 4,530,904, discloses a method for protecting bacteria in general from different types of bacteriophage. The method involves transforming a bacterium with a recombinant DNA cloning vector comprising a replicon that is functional in the bacterium, a gene that expresses a functional polypeptide (i.e., human growth hormone) in the bacterium, and a DNA segment which confers restriction and modification activity to the bacterium. The transformed bacterium is then cultured under large-scale fermentation conditions. This method is particularly adapted to fermentation procedures for the production of polypeptides such as growth hormone.

U.S. Pat. No. 4,732,859 to Hershberger et al. relates to a method of protecting various genera of bacteria from naturally occurring bacteriophage by providing host bacterial cells with a restriction system that digests HhaII site-containing foreign DNA (found in most naturally occurring phages) and renders the bacteriophage non-functional. Bacteria are transformed with a recombinant DNA cloning vector which comprises a gene that expresses a restriction endonuclease which confers restriction activity to the bacteria.

U.S. Pat. Nos. 4,918,014 and 4,874,616, both to Vedamuthu, are directed to a method of imparting bacteriophage resistance to bacteriophage sensitive strains of Lactococcus, whereby a plasmid encoding the production of a mucoid substance is conjugally transferred via a plasmid into a bacteriophage sensitive strain. Additional strategies used for the construction of bacteriophage-insensitive strains include the introduction of one or more resistance mechanisms within a single host, or introducing a single plasmid containing more than one resistance mechanism. For recent reviews, see Klaenhammer, T. R., *FEMS Microbiol. Rev.* 46:313–325 (1987); Sanders, *Biochimie* 70: 411–422 (1988); and C. Hill, *FEMS Microbiol. Rev.* 12, 87–108 (1993).

Plasmids and plasmid derivatives which confer bacteriophage restriction and modification (R/M) activity to lactococci containing the plasmid or derivative are described in U.S. Pat. Nos. 4,883,756, 4,931,396, 5,139,950, and 5,109,506.

Despite increased protection of starter cultures by rotation strategies or by use of phage resistant derivatives, new lytic bacteriophages appear routinely in industrial fermentations, disrupting the fermentative process and causing loss of substrates and products. Bacteriophages infecting Lactococcus strains have been classified into twelve distinct species (Jarvis, et al. *Intervirology*, 32:2(1991)). The lytic phages which have been the most prevalent in the dairy industry are classified in the species c2 and 936 and are composed of prolate- and small isometric-headed phages, respectively (Braun, et al. *J. Gen. Microbiol.* 135:2551(1992); Coveney et al., *Appl. Environ. Microbiol.* 53:1439(1987); Moineau, et al. *Can. J. Microbiol.* 38:875(1992)). More recently, another phage species, P335, has emerged with increasing frequencies in cheese plants (Alatossava and Klaenhammer. *Appl. Environ. Microbiol.* 57:1346(1991); Moineau, Pandian and Klaenhammer. *Appl. Environ. Microbiol.* 59:197(1993)).

The origin of new lactococcal bacteriophages in the dairy industry has been investigated, see, e.g., Davidson et al., *FEMS Microbiol. Rev.* 87:79 (1990); Jarvis, *J. Dairy Sci.,* 72:3406(1989). The genetic events believed to contribute to the evolution of new phage strains are infrequent, complex, and in general remain to be elucidated.

SUMMARY OF THE INVENTION

A first aspect of the present invention is a method of identifying a bacterial DNA sequence capable of recombining with DNA of a predetermined bacteriophage. The method may be used to identify bacterial DNA that contributes to the evolution of new bacteriophage which are resistant to a bacteriophage defense mechanism which previously protected a bacteria from the parent, or ancestor, bacteriophage from which the new bacteriophage evolved. Such bacterial DNA sequences are referred to as "bacteriophage evolutionary sequences" (or "BES"). The method comprises:

(a) introducing a bacteriophage defense mechanism into a bacterium (e.g., a gram-negative or gram-positive bacterium);

(b) culturing the bacterium in the presence of a first lytic bacteriophage (e.g., P335 bacteriophages, c2 bacteriophages, 936 bacteriophages, etc.) to produce a bacterial culture, the first lytic bacteriophage being sensitive to the bacteriophage defense mechanism;

(c) isolating from the bacterial culture a second lytic bacteriophage which is resistant to the bacteriophage defense mechanism;

(d) identifying DNA sequences present in the second lytic bacteriophage which are not present in the first lytic bacteriophage; and then (e) identifying a bacterial DNA sequence which is homologous to a DNA sequence of the second lytic bacteriophage identified in step (d) (i.e., a bacteriophage evolutionary sequence, or "BES"), wherein the identified bacterial DNA sequence is capable of recombination with DNA of the first lytic bacteriophage.

A second aspect of the present invention is a method of producing a recombinant bacterium for use in producing fermentative culture medium resistant to the appearance of new bacteriophage, the method steps (a) to (e) as set forth above, followed by the steps of:

(f) cloning or inserting the homologous DNA sequence into an integration vector such as a plasmid capable of homologous recombination with the bacterium chromosomal DNA and incapable of replication in the bacterium;

(g) inserting the integration vector into the bacterium; and (h) selecting a recombinant bacterium in which the recombinant bacterium has undergone homologous recombination with the integration vector, such that the identified bacterial sequences are disrupted in the recombinant bacterium.

The identified bacterial sequences may be disrupted by any suitable means, including insertion of an intervening sequence therein, or simply by deletion thereof. The recombinant bacterium so produced may be cultured to provide a fermentative culture or bacterial starter culture resistant to the appearance of new bacteriophage strains.

A third aspect of the present invention is a recombinant bacterium for use in producing fermentative culture medium resistant to the appearance of new bacteriophage, the recombinant bacterium containing a disrupted bacteriophage evolutionary sequence. Disruption may be carried out by any suitable means, as described above.

A fourth aspect of the present invention is the starter cultures produced as described above. The starter culture may be provided in any suitable form, including as a pure culture or a mixed culture. Typical starter cultures are those capable of fermenting a food substrate such as milk.

The foregoing and other objects and aspects of the present invention are explained in detail in the drawings herein and the sepecification set forth below.

DETAILED DESCRIPTION OF THE INVENTION

1. Appearance of New Bacteriophage

Figure 1:
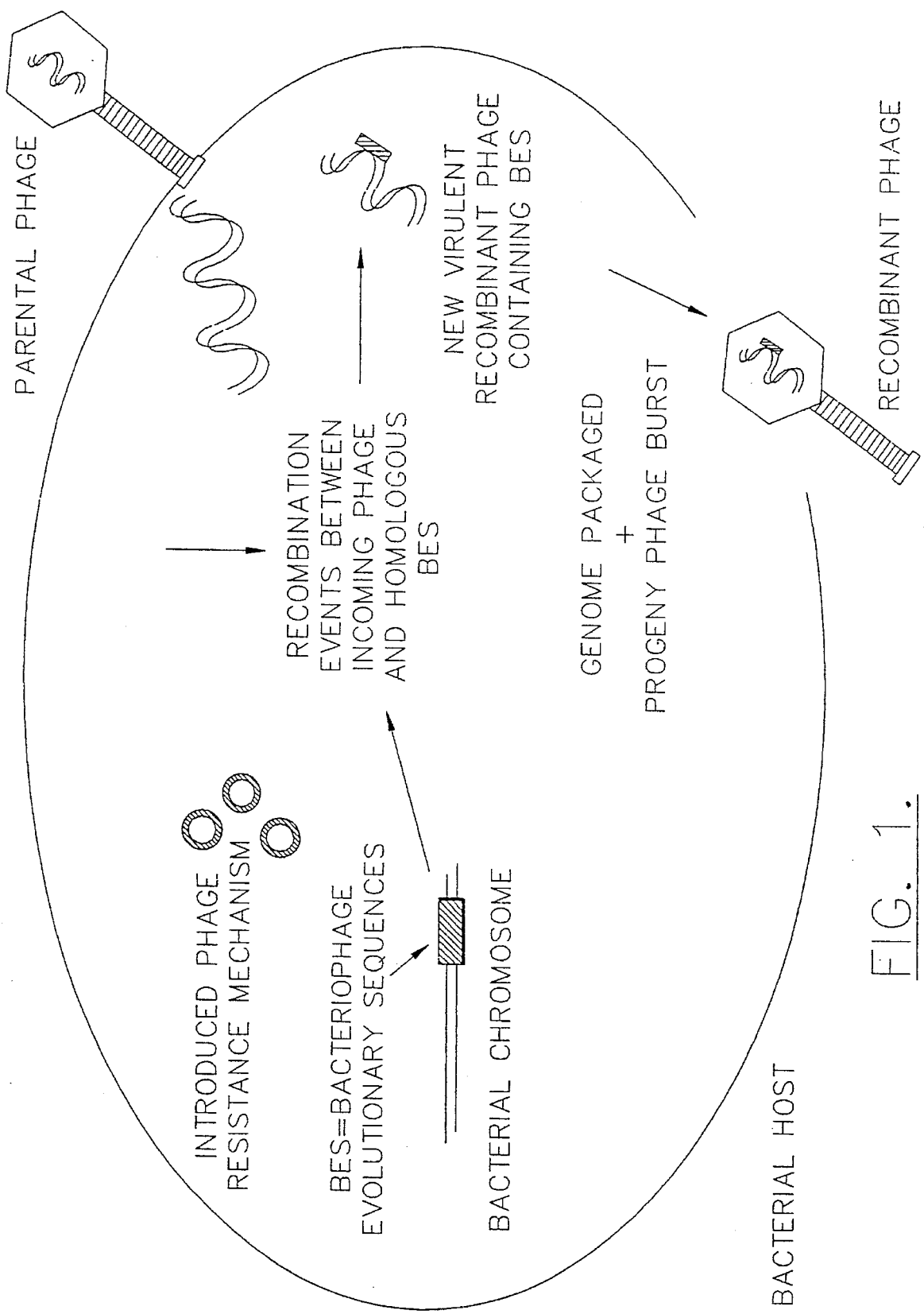
FIG. 1 diagrams the emergence of a recombinant lytic phage comprising a bacteriophage evolutionary sequence from a host bacterial chromosome.

It has been shown that raw milk contains phages which survive pasteurization. This natural reservoir can introduce new phages into the cheese plant environment (see, e.g., Mcintyre, et al. *Int. Dairy J.*, 1:183(1991)). Heteroduplex DNA studies have indicated that lytic phages may evolve from other lytic phages (Jarvis and Meyer., *Appl. Environ. Microbiol.*, 51:566(1986); Loof and Teuber. *Syst. Appl. Microbiol.*, 8:226(1986)). Consequently, DNA cassette exchanges between existing lytic phages has been proposed as one mechanism for appearance of new virulent phages in raw milk and cheese plants. It has also suggested that lysogenic starter cultures may be a source of new virulent phages (see, e.g. Davidson et al., *FEMS Microbiol. Rev.*, 87:79(1990)). However, DNA—DNA hybridization studies between lytic (mainly c2 and 936 species) and temperate phages have showed no significant homology (Braun, et al. *J. Gen. Microbiol.* 135:2551(1989); Relano, et al. *J. Gen. Microbiol.* 133:3053(1987)). These observations led to the current theory that temperate phages do not contribute significantly to the emergence of new virulent phages (Davidson, et al. *FEMS Microbiol. Rev.* 87:79–90(1990); Jarvis. *J. Dairy Sci.*, 72:3406(1989)).

As used herein, lytic bacteriophage are those bacteriophage that lyse the host cell after the initial infection in order to release new phage particles. In contrast, in temperate or lysogenic bacteriophage, the phage DNA can be retained in a bacterium for multiple cell divisions. Temperate phage DNA may be integrated into the host genomic DNA as a prophage or replicate lytically and lyse the host cell.

Recently, it has been reported that some lytic phages from P335 species have homology with temperate phages, suggesting that some temperate and lytic phages may have common ancestors (D'Amelio and Klaenhammer, unpublished data); Lautier and Novel, *J. Ind. Microbiol.* 2:151–158(1987); Moineau, Pandian and Klaenhammer, *Appl. Environ. Microbiol.*, 59:197(1993). Since a direct correlation between resident prophages and the appearance of new lytic phages has not been made in lactococci, the role of lysogenic strains as a source of lytic phages remains unclear (Davidson, Powell and Hillier, *FEMS Microbiol. Rev.* 87:79(1990); Jarvis. *J. Dairy Sci.* 72:3406(1989); Reyrolle, et al. *Appl. Environ. Microbiol.* 43:349(1982).

2. Bacteriophage Defense Mechanisms

Numerous bacteriophage-defense mechanisms are found in naturally occurring phage-resistant *Lactococcus lactis* strains (see T. Klaenhammer, *J. Dairy Sci.* 72, 3429 (1989); Coffey et al. *ASM, Washington, D.C.* 131 (1991)). They are classified into three categories based on their mode of action: prevention of adsorption (Ads), restriction and modification of incoming phage (R/M), and abortive infection (Hsp). Plasmid pTR2030 is a well-characterized example of a selected phage-defense mechanism introduced by conjugation into industrial strains (T. Klaenhammer, et al. *ASM,*

*Washington, D.C.* 124 (1991); U.S. Pat. No. 4,931,396) (the disclosures of all U.S. patents referenced herein are specifically intended to be incorporated herein in their entirety). See also M. Sanders et al., *Appl. Environ. Microbiol.* 52, 1001 (2986). Plasmid pTR2030 harbors at least two different phage-resistance mechanisms, a R/M system and an abortive infection system. Following its introduction in the cheese industry, phages resistant to the defense mechanisms of pTR2030 were isolated. Molecular analysis revealed that these new industrial phages belonged to the P335 species (Alatossava and Klaenhammer, *Appl. Environ. Microbiol.*, 57:1346(1991); Moineau, Pandian and Klaenhammer, *Appl. Environ. Microbiol.*, 59:197(1993)). However, study of the origin of these phages has proven difficult because of the unknown identity of their ancestors.

Another example of a selected plasmid encoded phage defense mechanism is the conjugative plasmid pTN20. One of the defense mechanisms present on pTN20 is PrF (AbiC) which codes for an abortive phage resistance mechanism (Durmaz et al., *J. Bacteriol.*, 174:7463(1992)). Of the industrial P335 phages isolated recently for *Lactococcus lactis* NCK203, only ul36 was sensitive to Prf (Moineau, Pandian and Klaenhammer, *Appl. Environ. Microbiol.*, 59:197(1993)).

3. Evolution of Phages with Bacterial DNA

Prf-resistant (Prf$^r$) phage derivatives were isolated and characterized by the present inventors after ul36 infected *L. lactis* NCK203 harboring the Prf abortive mechanism. Unexpectedly, the present inventors found that the resistant phage (ul37) was composed of DNA from phage ul36 and the chromosome of NCK203, indicating that DNA sequences in the host chromosome can contribute to the appearance of a new lytic phage.

The present inventors found that when the small isometric-headed bacteriophage ul36 (P335 species) infected *L. lactis* NCK203 harboring the abortive mechanism Prf, at least two distinct progeny phages were released: ul36 and ul37. Phage ul37, a new Prf$^r$ recombinant phage, differed from phage ul36 in its morphology, antibody reaction and genomic organization. DNA hybridization experiments and integration events that disrupted resident host sequences demonstrated that ul37 was composed of DNA from ul36 and the chromosome of NCK203. Three events were responsible for the appearance of phage ul37: infection by the lytic phage ul36, selective pressure by a Prf$^+$ defense, and the contribution of a DNA fragment from the NCK203 chromosome (FIG. 1).

While *L. lactis* NCK203 harbors at least one inducible prophage in its chromosome, the evidence gathered by the present inventors indicated that this prophage did not contribute to the emergence of ul37. First, electron microscopy analysis has shown that the base plate of ul37 was distinctive from both ul36 and the temperate phage (prophage). Second, in Southern hybridization analysis the intensity of ul37 hybridizing signals were stronger to chromosomal sequences and weaker to the prophage. Lastly, site-specific integration of ul37 DNA fragment into NCK203 chromosome did not eliminate prophage induction, but prevented the emergence of ul37-type phages. The presence of multiple prophages in the *L. lactis* genome has been reported previously (see, e.g., Chopin, et al., *Appl. Environ. Microbiol.*, 55:1769(1989); Jarvis et al., *Can. J. Microbiol.*, 38:398(1992)) and another resident prophage could contribute sequences to this process. However, no other temperate phages have been detected following exposure of NCK203 to mitomycin C or UV. Electron microscopy of MC-induced lysates revealed only one morphological phage type.

In the evolution of ul37, participation of DNA sequences from a non-inducible or defective prophage in NCK203 cannot be ruled out. Such sequences do not originate from the P335 species since the DNA acquired by ul37 does not hybridize with phage P335 DNA (Jarvis, et al., *Intervirology*, 32:2(1991). The fact that ul37 shows a different Per (phage encoded resistance) phenotype (Per50$^r$) and has a different base plate than ul36, supports the hypothesis that another prophage present in the chromosome of NCK203 contributes to the appearance of ul37. Since phage ul36 propagation is severely limited in Per50$^+$ NCK203 cells, ul36 probably contains an origin of replication (ori) similar to phage $\phi$50 (Hill et al., *J. Bacteriol.*, 172:6419(1990)). However, ul37 can propagate normally on Per50$^+$ NCK203 cells, suggesting that ul37 has a different origin of replication (ori) (see Example 7 for more details). Accordingly, the different base plate of ul37 and a new origin of replication could come from a second prophage residing in NCK203. Thus, the recombination event responsible for the emergence of ul37 upon Prf selective pressure yielded at least three important but seemingly independent changes: a Prf resistance phenotype, a new base plate and a different origin of replication. The present inventors have found that the acquisition by ul36 of one large DNA fragment from the *L. lactis* NCK203 chromosome via a cassette exchange accounts for the appearance of ul37.

A series of P335 phages was isolated following the introduction of pTR2030 into industrially important strains (Alatossava and Klaenhammer, *Appl. Environ. Microbiol.*, 57:1346(1991); D'Amelio and Klaenhammer, unpublished data) and it was postulated that these lactococcal phages represented a new emerging phage species (Moineau et al., *Appl. Environ. Microbiol.*, 59:197(1993)). This hypothesis was based on the high proportion of restriction sites in their genome compared to other lytic phages (936 and c2 species) which historically have been more commonly found in cheese plants.

The data of the present inventors strongly supports the emergence of new P335 phages. Phage ul37 is a member of the P335 species and has many restriction sites in its genome. Phage ul37 is a new phage that evolved through a previously unknown route in response to strong selective pressure. The industrial P335 phages recently isolated in the present inventors' laboratory are sensitive to either Per31 or Per50 (O'Sullivan, Hill and Klaenhammer, *Appl. Environ. Microbiol.*, 59:2449(1993)). Phage ul37 replication is not affected by either phage origin of replication (ori) in trans. The fact that phages $\phi$31, $\phi$50 and now ul37 have emerged with seemingly distinct origins of replication suggest that similar genetic exchange events may occur widely. Yap and Kruzer, *Proc. Natl. Acad. Sci.*, 88:6043(1991) have reported that phage origins of replication can serve as sites for genetic recombination.

4. Discussion

The absence of correlations between ancestors and new virulent phages has impaired the study of routes for phage evolution in the dairy industry. Recently, Hill et al., *J. Bacteriol.* 173:4363(1991) reported that an industrial lactococcal phage had acquired part of a methylase from plasmid pTR2030 to overcome strong selective pressure from a restriction/modification system. The direct ancestor of this phage isolate is unknown.

The present inventors have shown that lactococcal phage can exploit genetic elements from the host chromosome to avoid abortive pressure from a plasmid-borne phage defense mechanism, and have established a direct link between a progenitor phage (ul36) and a new lactococcal virulent phage (ul37).

The present inventors have shown that new lytic phages can evolve through the acquisition of bacterial host DNA (see FIG. 1). The present invention encompasses a process whereby bacterial DNA sequences that contribute to the evolution of such new lytic bacteriophages are first identified and then disrupted. When bacterial host strains that have specialized phage defense mechanisms are cultured, new virulent phages can emerge and overcome the engineered resistance mechanisms. In the present invention, these new phages are selected and characterized using known techniques. The genomes of the parental phage and the new virulent phages are compared by standard genetic techniques to identify new DNA sequences that have been acquired by the virulent phages. These sequences are further examined for homology to the chromosome of the host bacteria. DNA fragments acquired by the recombinant phage from the bacterial genome (herein termed bacteriophage evolutionary sequences or BES) are cloned into a "suicide" integration vector appropriate for the specific host. The vector is incapable of replication in the host and is inserted into the bacterial host using known techniques (e.g., by electroporation) and transformants are selected by standard screening procedures. Transformants are host bacterial cells where the vector DNA has been inserted in the bacterial chromosome via homologous recombination within the targeted bacterial DNA sequence. Transformants are selected and evaluated to identify those bacterial clones that no longer yield new recombinant phages when challenged with lytic phage. In these transformants, insertional disruption of the host bacteriophage evolutionary sequences prevents the appearance of new recombinant phages that evolve by acquisition of bacterial DNA (BES). As used herein, the term bacterial evolutionary sequences refers to a DNA sequence which is present in a bacterial host genome and which is able to recombine with bacteriophage DNA to produce a new bacteriophage genotype.

Using the above described strategy, the present inventors found that integration events directed into bacterial chromosome sequences, which were homologous to those found in phage ul37, prevented the appearance of the recombinant phage ul37. Integration of a recombinant plasmid (pTRK333::ul37) disrupted the genetic exchange processes responsible for the formation of ul37. Homologous recombination in the *L. lactis* chromosome has been used by other workers to stabilize industrially important genes (see, e.g., Casey, Daly and Fitzgerald, *Appl. Environ. Microbiol.*, 58:3283(1992); Leenhouts, et al., *Appl. Environ. Microbiol.*, 55:2568(1991)). Chopin et al. demonstrated that integration of foreign DNA into a prophage genome present in *L. lactis* IL1403 eliminated the inducibility of the residing prophage (*Appl. Environ. Microbiol.*, 55:1769(1989)).

While the present integration strategy prevented the appearance of ul37, ul36 Prf$^r$ phage could still be selected. These Prf$^r$ phages were identical to ul36 in DNA restriction pattern suggesting that minor DNA modifications yielded these Prf$^r$ phages. The same observation (Prf insensitivity without gross genetic modification) was reported with phages of the 936 species after infection of *L. lactis* LM0230 harboring Prf (Durmaz et al., *J. Bacteriol.*, 174:7463(1992)). Phage ul36 thus followed two independent routes to counteract the Prf defense mechanism: (a) a simple mutational response, and (b) an exchange of DNA modules between ul36 and the host chromosome.

The strategy employed by the present inventors may be used to prevent the appearance of new phages due to the elucidated genetic recombination route. A similar phenomenon where host chromosomal sequences are acquired during phage evolution has been discovered for another unrelated phage when placed under pressure by a different abortive phage resistance mechanism in the NCK203 background (O'Sullivan, Hill and Klaenhammer, *Appl. Environ. Microbiol.*, 59:2449(1993)). Preliminary data have also shown that DNA sequences present in ul37 and *L. lactis* NCK203 are also present in *L. lactis* IL1403 (data not shown). These data indicate that lactococcal phages of the P335 species generally use chromosomal DNA sequences to adapt or evolve. Use of the present methods to disrupt the contributing sequences from the host chromosome by various disruption strategies (e.g., insertion, deletion) can minimize evolutionary events responsible for phage adaptation to restrictive pressures. Neutralization of host sequences involved in phage evolution would extend the longevity of that strain in industrial use. An advantage of the instant invention is that, once the BES is identified, numerous strategies for disrupting the BES (e.g., insertional strategies, deletion strategies) will be readily recognized by those skilled in the art, and may be carried out by any suitable means so long as the disrupted BES is incapable of providing to bacteriophage resistance to the bacterial cell phage defense mechanism which would have otherwise been imparted thereby.

5. Fermentative Microorganisms

It will be apparent to those skilled in the art that the present methods are not limited to use in *L. lactis*, as any phage/host interaction in which BES are present and contribute to the appearance of new bacteriophage would be susceptible to the present strategy for eliminating genetic routes for bacteriophage evolution.

The art of fermentation is well known and the instant method is operable in a wide variety of fermentation processes.

While the present invention is, in a preferred embodiment, directed to the fermentation of food, the invention may be practiced with any fermentation process susceptible to disruption by bacteriophage infection, including processes for the production of antibiotics, amino acids, and solvents. Products produced by fermentation which are known to have encountered bacteriophage infection, and the corresponding infected fermentation bacteria, include Cheddar and cottage cheese (*Lactococcus lactis*, *Lactococcus cremoris*), Yogurt (*Lactobacillus bulgaricus*, *Streptococcus thermophilus*), Swiss cheese (*S. thermophilus*, *Lactobacillus lactis*, *Lactobacillus helveticus*), Blue cheese (*Leuconostoc cremoris*), Italian cheese (*L. bulgaricus*, *S. thermophilus*), Viili (*Lactococcus cremoris*, *Lactococcus lactis* subsp. *diacetylactis*, *Leuconostoc cremoris*), Yakult (*Lactobacillus casei*), casein (*Lactococcus cremoris*), Natto (*Bacillus subtilis* var. *natto*), Wine (*Leuconostoc oenos*), Sake (*Leuconostoc mesenteroides*), Polymyxin (*Bacillus polymyxa*), Colistin (*Bacillus colistrium*), Bacitracin (*Bacillus licheniformis*), L-Glutamic acid (*Brevibacterium lactofermentum*, *Microbacterium ammoniaphilum*), and acetone and butanol (*Clostridium acetobutylicum*, *Clostridium saccharoperbutylacetonicum*). See generally M. Sanders, Bacteriophages of Industrial Importance, in PHAGE ECOLOGY, 211–44 (S. Goyal, C. Berba and G. Bitton eds. 1987). Thus, the present invention may, for example, be employed in a fermentation process for producing any of the foregoing products with the foregoing bacteria in the manner described herein.

Bacteria capable of fermenting foods include those bacteria used in any type of food fermentation, including, but not limited to, the fermentation of milk, egg, meat, fruit, vegetables, and cereals. See generally Food Biotechnology, (D. Knorr Ed. 1987)(Marcel Dekker, Inc.); Fermented Foods (A. Rose Ed. 1982)(Academic Press); C. Pederson, Microbiology of Fermented Foods, (2d ed. 1979)(AVI Publishing Co.).

Milk is fermented to produce products such as cheese, yoghurt, kefir, and acidophilus milk. Cheese fermentation bacteria are discussed separately below. Otherwise, bacteria used for the fermentation of milk include, but are not limited to, *Lactobacillus bulgaricus, Lactobacillus acidophilus, Streptococcus thermophilus*, and mixtures thereof. See Food Biotechnology, 530 (D. Knorr Ed. 1987); C. Pederson, Microbiology of Fermented Foods, 105–35 (2d ed. 1979).

Bacteria used for the fermentation of milk to produce cheese include, but are not limited to, *Lactobacillus bulgaricus, Lactobacillus helveticus, Streptococcus thermophilus, Lactococcus lactis, Lactococcus cremoris, Lactococcus lactis* subsp. *diacetylactis*, and mixtures thereof. See Food Biotechnology, 530 (D. Knorr Ed. 1987); C. Pederson, Microbiology of Fermented Foods, 135–51 (2d ed. 1979).

Bacteria used for the fermentation of egg include *Pediococcus cerevisiae, Lactobacillus plantarum*, and mixtures thereof. See Food Biotechnology, 538–39 (D. Knorr Ed. 1987).

Bacteria used for the fermentation of meat (including beef, pork, and poultry) include, but are not limited to, Lactic acid bacteria, *Pediococcus acidilactici, Lactobacillus plantarum, Lactobacillus brevis*, Micrococcus species, *Leuconostoc mesenteroides*, and mixtures thereof. See Food Biotechnology, 538–39 (D. Knorr Ed. 1987); C. Pederson, Microbiology of Fermented Foods, 210–34 (2d ed. 1979); U.S. Pat. No. 2,225,783 to Jensen and Paddock.

Bacteria used for the fermentation of vegetables (e.g., carrots, cucumbers, tomatoes, peppers, and cabbage) include, but are not limited to, *Lactobacillus plantarum, Lactobacillus brevis, Leuconostoc mesenteroides, Pediococcus pentosaceus*, and mixtures thereof. See Food Biotechnology, 540 (D. Knorr Ed. 1987); C. Pederson, Microbiology of Fermented Foods, 153–209 (2d ed. 1979); U.S. Pat. No. 3,024,116 to Engelland; U.S. Pat. No. 3,403,032 to Etchells et al.; U.S. Pat. No. 3,932,674 to Etchells et al.; U.S. Pat. No. 3,897,307 to Porubcan et al.

Bacteria used in the fermentation of dough formed from cereals (e.g., wheat, rye, rice, oats, barley, and corn) include yeasts such as *Saccharomyces cerevisiae* and *Candida utilis*; and lactic acid bacteria of the genera Lactobacillus, Lactococcus, Pediococcus and Leuconostoc, including, but not limited to *Lactobacillus delbrueckii, Lactobacillus leichmanni, Lactobacillus plantarum, Lactobacillus casei, Lactobacillus brevis, Lactobacillus fermenti, Lactobacillus pastorianus, Lactobacillus buchneri*, and *Leuconostoc mesenteroides*. See generally Food Biotechnology, 235–70 (D. Knorr Ed. 1987); U.S. Pat. No. 3,734,743 to Kline and Sugihara; U.S. Pat. No. 3,681,083 to Everson; U.S. Pat. No. 3,993,783 to Khoudokormoff and Langejan; U.S. Pat. No. 3,843,800 to Langejan; U.S. Pat. No. 3,410,692 to Wutzel.

Wine is produced by the fermentation of fruit juice, typically grape juice, with yeasts, such as *Saccharomyces cerevisiae* and *Saccharomyces ellipsoideus*, as well as with a broad variety of lactic acid bacteria including *Pediococcus pentosaceus, Lactobacillus plantarum, Leuconostoc mesenteroides* subsp. *dextranicum* and subsp. *cremoris, Lactobacillus brevis*, and *Lactobacillus fermenti*. Beer is produced by the fermentation of malt with yeasts such as *Saccharomyces cerevisiae* and *Saccharomyces carlsbergensis*. See C. Pederson, Microbiology of Fermented Foods, 271–309 (2d ed. 1979).

In a particularly preferred embodiment, the present invention is employed for the fermentation of milk with lactococci (previously classified as the group N Streptococci), such as *Lactococcus lactis* subsp. *lactis, Lactococcus lactis* subsp. *cremoris*, and *Lactococcus lactis* subsp. *lactis* biovar. *diacetylactis* (also called *Lactococcus diacetylactis*).

A further aspect of the present invention relates to a defined bacterial starter culture capable of fermenting a predetermined product. The bacterial starter culture comprises the modified bacteria described herein. The use of modified host bacteria in a starter culture increases the longevity of the culture by inhibiting or forestalling the evolution of new phages comprising BES. The end result is a more economical fermentation process on an industrial scale. Bacterial starter cultures comprising the modified bacteria can be used in the fermentation of a variety of products as described above. A preferred bacterial species is the Lactococcus, and preferred species are *L. lactis* subsp. *lactis* and *L. lactis* subsp. *cremoris*.

The bacterial starter culture may consist of one bacterial strain, i.e., a pure culture. In this case substantially all, or at least a significant portion of the bacterial starter culture would generally comprise the modified bacterial cells. In the alternative, the starter culture may comprise several bacterial strains, i.e., a defined mixed culture wherein a portion of each bacterial strain is modified in accordance with the instant invention. The preferred situation in either case would be to provide starter cultures wherein substantially all the bacterial cells are modified in order to eliminate defined genetic routes for bacteriophage evolution.

A further aspect of the present invention contemplates a method of conducting a fermentation of a product employing a bacterial starter culture of the instant invention. A fermentation process using the transformed bacteria of the present invention may be conducted on a less interrupted basis since the problems of bacteriophage evolution and infection, and subsequent lysis of a predominant portion of the initial bacterial starter culture, are alleviated. For example, as explained in Example 10 below, use of plasmid pTRK333::ul37 in NCK203 host cells prevented the appearance of ul37. Starter cultures of the present invention will produce fermentative cultures which are resistant to the appearance of new bacteriphage, i.e., cultures in which at least one genetic route for the evolution of new bacteriophage has been eliminated.

Starter cultures employed in practicing the present invention may be in any physical form, including liquid cultures of the fermentation bacteria in a suitable growth medium, as well as lyophilized cultures and frozen cultures prepared therefrom.

Fermentation vessels used to prepare the starter cultures or conduct fermentation using methods of the present invention depend upon the stage of the fermentation and the substrate or media being fermented. Suitable vessels include both sealed sterile vessels, closed bulk culture vessels, and open, nonsterile vessels or fermentation vats. The instant invention is particularly suitable for use in fermentations carried out under nonsterile conditions where phage infection is more likely.

The fermentation apparatus and conditions under which fermentation should be conducted may be selected and determined, respectively, by persons of ordinary skill in the art so as to produce the desired product while maintaining the viability of the transformed bacteria in the starter culture.

6. Vectors

A further aspect of the present invention relates to a recombinant DNA vector comprising a BES of a predetermined bacterial host, wherein the vector is incapable of autonomous replication in the predetermined bacterial host.

Any vector capable of integrating into the host chromosome DNA can be used in accordance with the present invention, as discussed below.

Figure 2:
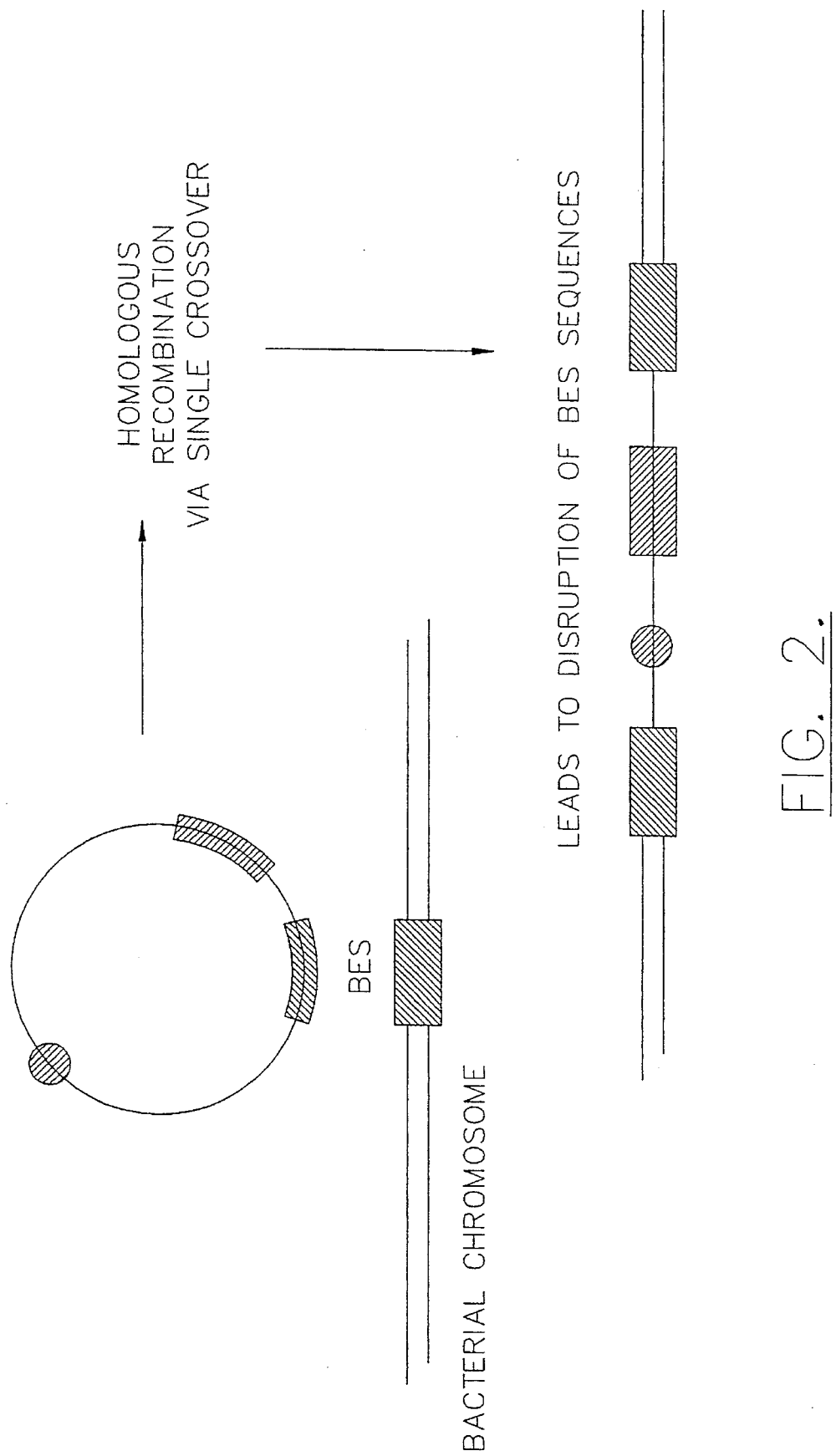
FIG. 2 diagrams the use of a suicide integration vector to disrupt a bacteriophage evolutionary sequence in a bacterial chromosome.

Vectors useful for practicing the present invention include plasmids, viruses (including phage), and integratable DNA fragments (i.e., fragments integratable into the host bacterial genome by homologous recombination or transposition). The vectors of the present invention are suicide vectors; as used herein, suicide vector refers to a vector that is unable to replicate in a predetermined host. Construction of a suicide vector may be accomplished, as described herein at Example 9, by engineering a vector deficient in an origin of replication appropriate for the intended host (e.g., an integration vector for use in a gram-positive bacterial host will lack a gram-positive origin of replication). Vectors of the present invention are integratable vectors carrying bacterial evolutionary sequences from a predetermined host bacterium and unable to replicate in the host when integrated in the host genome. Vectors may optionally contain selection genes, such as gene encoding proteins conferring antibiotic resistance or supplying an autotrophic requirement. The DNA of the vector integrates into the host chromosome by homologous recombination, leading to disruption of the BES in the host chromosome (FIG. 2). Modified host cells are bacterial cells which have been transformed with the vectors of the present invention.

Suitable host cells include gram-negative or gram-positive organisms such as Lactococcus, *Escherichia coli* (*E. coli*) or Bacilli. The construction of suitable vectors for use in the present method will depend upon the intended host cell and the virulent phages encountered by that host cell in its intended industrial use. The requirements of a vector, given its intended host, will be readily determined by those skilled in the art.

In an illustrative embodiment, the recombinant vector is the plasmid designated pTRK333, the preparation and analysis of which are set forth in the Examples.

The present invention is explained in greater detail in the examples which follow. These examples are set forth for illustrative purposes only, and are not to be taken as limiting. In the following examples, ° C. means degrees Centigrade, μg means microgram, μl means microliter, ml means milliliter, mg means milligram, mM means milliMolar, EOP means Efficiency of Plating, nm means nanometer, g means gravity, μm means micron, rpm means revolutions per minute, M means Molar, μF means microFarad, kV means kilovolt, μCi means microCurie, and cfu means colony forming units.

EXAMPLE 1

Materials and Methods

1. Bacterial Strains, Plasmids and Media. The strains and plasmids used in this study are listed in TABLES 1 and 2. *Escherichia coli* was grown at 37° C. in LB broth or agar (Maniatis et al, *Molecular cloning: a laboratory manual*, Cold Spring Harbor Laboratory, Cold Spring Harbor, N.Y. (1982)). *L. lactis* strains were grown at 30° C. in M17 broth or agar (Terzaghi and Sandine, *Appl. Microbiol.*, 29:807(1975)) with 0.5% glucose (GM17). When appropriate, antibiotics were added as follows: for *E. coli*, 50 μg/ml ampicillin, 10 μg/ml tetracycline; for *L. lactis*, 2 μg/ml erythromycin and 5 μg/ml chloramphenicol.

2. Bacteriophage Propagation. All phages, including ul36, were isolated from a single plaque. Plaques were picked with a 1 ml sterile pipette and transferred to GM17+10 mM $CaCl_2$, inoculated (1%) previously with an overnight culture of the host strain. Bacteriophages were propagated and titered according to Jarvis (Jarvis, *Appl. Environ. Microbiol.*, 47:1031(1978). Efficiency of plaquing (EOP) assays were conducted as described by Sanders and Klaenhammer, *Appl. Environ. Microbiol*, 40:500(1980).

TABLE 1

| BACTERIA | | RELEVANT CHARACTERISTICS | SOURCE |
|---|---|---|---|
| *E. coli* | DH5a | Transformation host | Gibco/BRL |
| *L. lactis* | NCK203 | Lac–derivative of the industrial strain LMA12 Propagating host for phage ul36, ul37, ø31, ø48, ø50. | 1* |
| | LM0230 | Lac–, host for 936 and c2 phages. | 2* |
| | MG1363 | Lac–, host for 936 and c2 phages. | 3* |
| | IL1403 | Lac–, host for 936 and c2 phages. | 4* |
| | c6 | Lac+, host for phage c6A (c2 species). | 5* |
| | 2704 | Lac+, host for 936 phages, industrial strain. | 6* |
| | 2404 | Lac+, host for c2 phgges, industrial strain. | 6* |
| | NCK279 | NCK203 (pTRK18), $Hsp^+$, $Em^r$. | This study |
| | NCK597 | NCK203 (pTRK340), $Ap^4$, $Tc^s$, $Cm^4$. | This study |
| | NCK599 | NCK203 (pTRK342), $Ap^4$, $Tc^s$, $Cm^4$. | This study |
| | NCK600 | NCK203 (pTRK343), $Ap^4$, $Tc^s$, $Cm^4$. | This study |
| | NCK601 | NCK203 (pTRK344), $Ap^4$, $Tc^s$, $Cm^4$. | This study |
| | NCK602 | NCK203 (pTRK345), $Ap^4$, $Tc^s$, $Cm^4$. | This study |
| | NCK603 | NCK203 (pTRK347), $Ap^4$, $Tc^s$, $Cm^4$. | This study |
| | NCK605 | NCK203 (pTRK340, pTRK99), $Prf^+$, $Ap^r$, $Tc^s$, $Cm^r$, $Em^r$. | This study |
| | NCK606 | NCK203 (pTRK342, pTRK99), $Prf^+$, $Ap^r$, $Tc^s$, $Cm^r$, $Em^r$. | This study |
| | NCK607 | NCK203 (pTRK343, pTRK99), $Prf^+$, $Ap^r$, $Tc^s$, $Cm^r$, $Em^r$. | This study |
| | NCK608 | NCK203 (pTRK344, pTRK99), $Prf^+$, $Ap^r$, $Tc^s$, $Cm^r$, $Em^r$. | This study |
| | NCK609 | NCK203 (pTRK345, pTRK99), $Prf^+$, $Ap^r$, $Tc^s$, $Cm^r$, $Em^r$. | This study |
| | NCK610 | NCK203 (pTRK347, pTRK99), $Prf^+$, $Ap^r$, $Tc^s$, $Cm^r$, $Em^r$. | This study |
| | NCK612 | NCK203 (pTRK323), Per50, $Em^r$. | 7* |
| | NCK620 | NCK203 (pTRK361), Pel31, $Em^r$. | 7* |
| | NCK644 | NCK203 (pTRK99), $Prf^+$, $Em^r$. | 8* |

TABLE 1-continued

| BACTERIA | RELEVANT CHARACTERISTICS | SOURCE |
|---|---|---|
| Bacteriophages | | |
| ul36 | SI, P335 species, Prf$^s$, Per50$^s$, Per31$^r$, 28.8 kb | 9* |
| ul37 | SI, P335 species, Prf$^r$, Per50$^r$, Per31$^r$, 31.1 kb | This study |
| ø31 | SI, P335 species, Prf$^r$, Per50$^r$, Per31$^r$, 31.9 kb | 10* |
| ø48 | SI, P335 species, Prf$^r$, Per50$^s$, Per31$^r$, 31.1 kb | 10* |
| ø50 | SI, P335 species, Prf$^r$, Per50$^s$, Per31$^r$, 29.8 kb | 10* |

LEGEND FOR TABLE 1:
Ap$^r$ = ampicillin resistance
Cm$^r$ = chloramphenicol resistance
Em$^r$ = erythromycin resistance
Tc$^s$ = sensitive to tetracycline
Lac+ = lactose-fermenting ability
Lac− = deficient in lactose-fermenting ability
Prf$^s$ = sensitive to Prf
Prf$^r$ = resistant to Prf
Per31$^s$ = sensitive to Per31
Per31$^r$ = resistant to Per31
Per50$^s$ = sensitive to Per50
Per50$^r$ = resistant to Per50
Sl = small isometric-head
1* Hill et al., Appl. Environ. Microbial., 55, 2416 (1989).
2* McKay et al., Appl. Environ. Microbiol., 23, 1090 (1972).
3* Gasson, J. Bacteriol, 154, 1 (1983).
4* Chopin et al., Plasmid, 11, 260 (1984).
5* Powell and Davidson, J. Gen. Microbiol., 66, 2737 (1985).
6* Moineau et al., FEMS Microbial. Lett., 92, 169 (1992).
7* O'Sullivan et al., Appl. Environ. Microbial., 59, 2449 (1993).
8* Durmaz et al., J. Bacteriol., 174, 7463 (1992).
9* Moineau et al., Can. J. Microbial., 38, 875 (1992).
10* Alatossava and Kiaenhammer, Api)l. Environ. Microbiol., 57, 1346 (1991).

TABLE 2

| Plasmids | Relevant characteristics | Source |
|---|---|---|
| pBR322 | Cloning vector in gram−, Ap$^r$, Tc$^r$, 4361 bp. | NEB |
| pGK12 | Shuttle vector, Em$^r$, Cm$^r$, 4378 bp. | 11* |
| pTRK18 | Hsp$^+$, abiA, Em$^r$, Cm$^r$, 10.1 kb. | 1* |
| pTRK99 | Prf$^+$, abiC, Em$^r$, Cm$^r$, 11.4 kb. | 8* |
| pTRK323 | Per50, Em$^r$. | 7* |
| pTRK361 | Per31, Em$^r$. | 7* |
| pTRK333 | Suicide vector in gram+, Ap$^r$, Tc$^r$, Cm$^r$, 5.8 kb. | This study |
| pTRK333::ul36 recombinant plasmids | | |
| pTRK334 | 3.4 kb HindIII fragment from ul36 cloned in the unique HindIII site (Tc gene) of pTRK333, Ap$^r$, Tc$^s$, Cm$^r$ | This study |
| pTRK335 | 2.8 kb HindIII fragment from ul36 cloned into pTRK333. | This study |
| pTRK336 | 2.4 kb HindIII fragment from ul36 cloned into pTRK333. | This study |
| pTRK337 | 2.0 kb HindIII fragment from ul36 cloned into pTRK333. | This study |
| pTRK338 | 1.6 kb HindIII fragment from ul36 cloned into pTRK333. | This study |
| pTRK339 | 1.5 kb HindIII fragment from ul36 cloned into pTRK333. | This study |
| pTRK340 | 1.4 kb HindIII fragment from ul36 cloned into pTRK333. | This study |
| pTRK341 | 1.2 kb HindIII fragment from ul36 cloned into pTRK333. | This study |
| pTRK333::ul37 recombinant plasmids | | |
| pTRK342 | 3.7 kb HindIII fragment from ul37 cloned into pTRK333. | This study |
| pTRK343 | 2.4 kb HindIII fragment from ul37 cloned into pTRK333. | This study |
| pTRK344 | 1.9 kb HindIII fragment from ul37 cloned into pTRK333. | This study |
| pTRK345 | 1.6 kb HindIII fragment from ul37 cloned into pTRK333. | This study |
| pTRK346 | 1.4 kb HindIII fragment from ul37 cloned into pTRK333. | This study |
| pTRK347 | 1.2 kb HindIII fragment from ul37 cloned into pTRk333. | This study |

LEGEND FOR TABLE 2:
abi = abortive mechanism
Ap$^r$ = ampicillin resistance gene
Tc$^r$ = tetracycline resistance gene
Cm$^r$ = chloramphenicol resistance gene
Em$^r$ = erythromycin resistance gene
NEB = New England Biolabs, Inc., Beverley, MA.
1* = Hill et al., Appl. Environ, Microbial., 55, 2416 (1989).
7* = O'Sullivan et al., Appl. Environ. Microbial., 59, 2449 (1993).
8* = Durmaz et al., J. Bacterial., 174, 7463 (1992).
11* = Kok et al., Appl. Environ. Microbiol., 48,726 (1984).

3. Prophage Induction. *L. lactis* NCK203 cells were grown in GM17 at 30° C. until the optical density at 600 nm reached 0.2. Mitomycin C (MC) was added to final concentration of 10 µg/ml. The culture was incubated for 100 minutes and prophage DNA was isolated according to Hill et al., *Appl. Environ. Microbiol.*, 57:283(1991).

4. Monoclonal Antibody Reactions. Production of monoclonal antibodies against the major capsid protein of ul36 and sandwich ELISA were as described elsewhere (Moineau, et al., *Appl. Environ. Microbiol.*, 59:2034(1993); Moineau, et al., *Appl. Environ. Microbiol.*, 59:208(1993)).

5. Electron Microscopy. Fresh bacterial lysates were centrifuged at 12,000×g for 10 minutes and filtered through 0.45 µm membrane filter (ACRODISC®, Gelman Sciences, Ann Arbor, Mich.). Phage particles were sedimented at 25,000 rpm (Beckman SW41.Ti) for 60 minutes. Pellets were gently washed twice in 0.1M ammonium acetate pH 7.2 and sedimented at 25,000 rpm for 30 minutes. Pellets were resuspended in 1 ml of 0.1M ammonium acetate pH 7.2, transferred to an Eppendorf tube and spun at 10,000 rpm for 10 minutes in a microcentrifuge. One drop of supernatant was deposited on a Formar grid and stained with 2% potassium phosphotungstate, pH 7.2. Excess liquid was adsorbed with filter paper. Specimens were visualized with a Philips 410 electron microscope. Dimensions were measured on photographic prints at a final magnification of 200,000×. Tail length was measured on intact phages only and included the base plate.

6. Bacterial DNA Isolation and Manipulation. Plasmid DNA from *E. coli* was isolated as follows. One ml from an overnight culture was centrifuged 5 minutes at 14,000 rpm in a microcentrifuge. The pellet was resuspended in lysis buffer (50 mM Tris-HCl pH 7.5, 1% SDS and 50 µg/ml RNase), held at room temperature for 10 minutes, and centrifuged at 14,000 rpm for 10 minutes. This pellet was lifted out with a toothpick and discarded. A 15 µl aliquot of the supernatant was electrophoresed on a 0.7% agarose gel. For electroporation or digestion with restriction endonucleases, the supernatant was extracted once with phenol/chloroform (1:1) and the DNA precipitated with 1/10 volume of 3M sodium acetate (pH 5.2) and 2.5 volumes of 95% ethanol. The DNA was resuspended in 10 µl of TE (50 mM Tris-HCl pH 7.5, 10 mM EDTA). One µl was used per electroporation and 5 µl per restriction enzyme digestion. When large quantities of *E. coli* plasmid DNA were needed, the DNA was isolated using QIAGEN® plasmid midi kit (Qiagen Inc., Chatsworth, Calif.). Plasmid DNA from *L. lactis* was isolated according to O'Sullivan and Klaenhammer, *Appl. Environ. Microbiol.*, 59:2730(1993). Chromosomal DNA from *L. lactis* was isolated according to Hill et al., *Appl. Environ. Microbiol.*, 57:283(1991).

7. Phage DNA Isolation and Manipulation. One ml of fresh phage lysate was centrifuged at 10,000 rpm for 10 minutes in a microfuge. One µl of RNase (1 mg/ml) and 1 µl of DNase (1 mg/ml) was added and incubated at 37° C. for 30 minutes. After centrifugation at 14,000 rpm for 10 minutes, the supernatant was transferred to another microfuge and 100 µl of SDS mix (0.5M Tris-HCl pH 9.0, 0.25M EDTA, 2.5% SDS) was added. The solution was mixed with a vortex for a few seconds and incubated at 65° C. for 30 minutes. Then 125 µl of 8M potassium acetate was added, mixed and placed on ice for 30 minutes. After centrifugation, the clear supernatant was aliquoted into two Eppendorf tubes and each sample extracted twice with phenol/chloroform. Phage DNA was precipitated with an equal volume of isopropanol and each pellet resuspended in 20 µl of water. Depending on the initial titer of the phage lysate, 10 or 20 µl was used per enzyme digest.

EXAMPLE 2

Construction of a Chloramphenicol-Based Gram-Positive Integration Vector

The 1.4 kb Sau3A fragment containing the chloramphenicol resistance gene from pGK12 (Kok, van der Vossen and Venema, *Appl. Environ. Microbiol.*, 48:726(1984)) was gel purified, recessed ends filled in with Klenow enzyme, and ligated to the unique, Klenow-filled, AvaI site of pBR322. The resulting 5.8 kb plasmid, pTRK333, contains a gram-negative origin of replication (G– ori), ampicillin (Ap$^r$) and tetracycline (Tc$^r$) resistance markers for selection in *E. coli*, and chloramphenicol resistance (Cm$^r$) for selection in lactococci. See FIG. 3, where G+ ori means gram-positive origin of replication; G– ori means gram-negative origin of replication; Rop means rop gene from the ColE1 derivative pMB1 involved in the regulation of the gram– ori; RepA means repA gene from pWV01 involved in the regulation of the G+ ori. Restriction enzymes, Klenow enzyme and T4 DNA ligase were obtained from Boehringer Mannheim (Indianapolis, Ind.) and used according to manufacturer's instructions. When needed, DNA fragments were isolated from low-melting agarose gel using QIAEX® gel extraction kit (Qiagen, Inc., Chatsworth, Calif.).

EXAMPLE 3

Electroporation

*E. coli* cells were grown at 37° C. for 6 hours in LB broth, centrifuged, washed twice in 0.5M sucrose+10% glycerol, and stored at −80° C. until used. *L. lactis* cells were propagated overnight at 30° C. in GM17+0.5M sucrose (SGM17) supplemented with the appropriate concentration of glycine, centrifuged, washed twice in 0.5M sucrose+10% glycerol, and stored at −80° C. according to Holo and Nes, *Appl. Environ. Microbiol.*, 55:3119(1989). *L. lactis* strains NCK203, IL1403 and 2404 cells were grown in 1% glycine, strains c6 and 2704 in 2% glycine, and strains LM0203 and MG1363 in 4% glycine. The GENE PULSER® (Bio-Rad Laboratories, Richmond, Calif.) was used set at 25 µF and 2.45 kV, and the pulse controller at 200 ohms. Plasmid DNA (1 µg) was mixed with 40 µl of cells in a chilled GENE PULSER® cuvette. After electroporation, *E. coli* cells were immediately resuspended in SOC medium and incubated 1 hour at 37° C. with shaking prior to plating on LB plates supplemented with the appropriate antibiotic (Maniatis, Fritsch and Sambrook, *Molecular cloning: a laboratory manual*, Cold Spring Harbor Laboratory, Cold Spring Harbor, N.Y. (1982)). *L. lactis* cells were resuspended in SGM17 and incubated 2 hour at 30° C. For integration experiments, *L. lactis* cells were incubated 18 hour at 30° C. prior to plating on SGM17+antibiotic.

EXAMPLE 4

Southern Hybridization

DNA was digested with restriction enzyme, electrophoresed on 0.7% agarose gel, and transferred onto nylon membranes (MSI, Westboro, Mass.) by the method of Southern, *J. Mol. Biol.*, 98:503(1975). DNA was fixed to the membrane with a UV-STRATALINKER® 1800 (Stratagene, La Jolla, Calif.). DNA probes were labeled with $^{32}$P-adCTP (NEN, Boston, Mass.) using the MULTIPRIME® DNA labelling system (Amersham, Arlington Heights, Ill.). A total of 50 µCi was used per labeling reaction. Unincorporated nucleotides were removed by NUCTRAP® push column (Stratagene, la Jolla, Calif.). Membranes were pre-hybridized, hybridized, washed and exposed as described previously (Moineau, Fortier and Pandian, *FEMS Microbiol. Lett.*, 92:169(1992)).

EXAMPLE 5

Pulse-Field Gel Electrophoresis (PFGE)

PFGE was performed according to Tanskanen et al., *Appl. Environ. Microbiol.*, 56:3105(1990) using PULSAPHOR® electrophoresis unit (Pharmacia-LKB, N.J.). Agarose (1.2%) gels were prepared in 0.5X TBE (0.045M Tris-borate, 0.001M EDTA). Running conditions were: 200 V, 1–20 second step switching time for 22h in 0.5X TBE. Lambda DNA-PFGE markers were used as DNA ladders (Pharmacia LKB, N.J.).

EXAMPLE 6

PRF Resistant Phage Isolation

*L. lactis* NCK203 is a Lac derivative of the industrial strain LMA12 which has been used extensively in commercial dairy fermentations. Phage ul36, a small isometric-headed phage of the P335 species, was first isolated from a Canadian cheese plant in 1990 (Moineau, et al., *Can. J. Microbiol.*, 38:875(1992)). Phage ul36 propagates on NCK203 and is sensitive to the plasmid-encoded abortive phage defense mechanism, Prf, encoded on pTRK99 (Durmaz et al., *J. Bacteriol.*, 174:7463(1992)).

The EOP of phage ul36 on Prf+ NCK203 (pTRK99) was $10^{-3}$; plaques were pinpoint relative to the normal plaques (1 mm) on the sensitive host NCK203 (data not shown). At an EOP of $10^{-5}$, larger plaques (1.5 to 2 mm) were observed in a lawn of Prf+ cells (data not shown). A few small and large plaques were picked and propagated on NCK203. These lysates were then tested on Prf+ cells of NCK203 (pTRK99). Phages purified from the small plaques were Prf sensitive (Prf$^s$); whereas the phages purified from the large plaques were Prf resistant (Prf$^r$) and formed large plaques on Prf+ cells at an EOP of 1.0.

EXAMPLE 7

Phage Characterization

The DNA of phage ul36 and its Prf$^s$ and Prf$^r$ derivatives were compared after digestion with various restriction enzymes. The DNA restriction pattern of the Prf$^s$ phage, which formed pinpoint plaques on NCK203 (pTRK99) was identical to ul36 (data not shown). In contrast, the DNA pattern of the Prf$^r$ phage was strikingly different from ul36, even though some common bands were evident. All Prf$^r$ phage isolates showed the identical DNA restriction pattern. The DNA pattern of the Prf$^r$ phage did not correspond to the DNA pattern of any phage in our collection; it was therefore designated as a new phage, ul37. DNA restriction patterns of ul36 and ul37 with four restriction enzymes were determined (data not shown). Certain bands were present in both phages, but new bands were detected in the Prf$^r$ phage ul37. On the basis of these various restriction fragments, the genome size of ul37 was estimated at 31.1 kb. The genome size of ul36 was estimated previously at 28.8 kb (Moineau, et al., *Can. J. Microbiol.*, 38:875(1992)). These data indicated that if ul37 is derived from ul36, major DNA rearrangements were responsible for the transition of the Prf$^s$ ul36 to its Prf$^r$ derivative, ul37.

Phages ul36 and ul37 were further characterized by the methods shown in TABLE 3 and TABLE 4. DNA—DNA hybridization analysis revealed that the genomes of ul36 and ul37 had homology to the genome of phage P335 (data not shown), prompting their classification into the P335 species (Jarvis, et al., *Intervirology*, 32:2(1991)). It was noteworthy that all the restriction fragments of ul36 hybridized with P335, whereas most, but not all, of the restriction fragments of ul37 hybridized. Electron microscopic analysis showed that both phages had isometric heads of 55 nm in diameter and a collar, but ul36 had a shorter tail (135 nm) than ul37 (150 nm). Monoclonal antibodies (Mabs) against the major capsid protein of ul36 were used in a sandwich ELISA with ul36 and ul37 (Moineau, et al., *Appl. Environ. Microbiol.*, 59:2034(1993)). Phage ul37 reacted with the Mabs raised against ul36 but to a lower degree than ul36 (TABLE 3). The most striking morphological difference between the two phages was their base plate. Phage ul36 exhibited a distinctive double base plate, whereas ul37 had a spike at the base plate. These genetic and morphological differences provided evidence that ul36 and ul37 are distinct phages. Even though both phages were classified in the same species there were variations between ul36 and ul37 at the phenotypic, genomic and structural protein levels.

Both phages were further characterized for phenotype by challenging them against the various defense mechanisms available in NCK203 derivatives (TABLE 4). Three different abortive mechanisms were used for this purpose: Hsp (Hill, et al., *Appl. Environ. Microbiol.*, 55:2416(1989), Per31 (O'Sullivan et al., *Appl. Environ. Microbiol.*, 59:2449(1993)) and Per50 (Hill et al., *J. Bacteriol.*, 172:6419(1990)). The naturally-occurring abortive mechanism Hsp (abiA) interferes with phage DNA replication (Hill et al., *Appl. Environ. Microbiol.*, 57:283(1991)). The abortive-type defense mechanisms Per31 and Per50 are composed of the origins of replication from the lactococcal phages φ31 and φ50 (P335 species), respectively, which have been cloned separately onto a high copy plasmid (O'Sullivan et al., *Appl. Environ. Microbiol.* 59:2449(1993)). When a phage infects a host harboring the same or nearly identical origin of replication, a competition for replication factors is proposed to occur between the incoming phage and the "false" phage origin cloned in trans. Phage ul36 is sensitive to the abortive mechanisms Prf, Hsp and Per50, but resistant to Per31, indicating that ul36 has a similar origin of replication to phage φ50. Phage ul37 was sensitive only to Hsp and was unaffected by per31, per50, and Prf suggesting that its origin of replication was distinct from phages ul36, φ31 and φ50.

TABLE 3

| Phage | Phage Species | Head Diam. | Tail Length | Genome Size | Mab Reaction[1] |
|---|---|---|---|---|---|
| ul36 | P335 | 55 nm | 135 nm | 28.8 kb | +++ |
| ul37 | p335 | 55 nm | 150 nm | 31.1 kb | + |

[1](+++) strong reaction; (+) weak reaction.

TABLE 4

| | EOP[1] of Phages on NCK203 Derivatives | | | |
|---|---|---|---|---|
| Phage | NCK644 Prf+ | NCK279 HSP+ | NCK612 Per50+ | NCK620 Per31+ |
| ul36 | $10^{-3}$ | $10^{-2}$ | $10^{-6}$ | 1 |
| ul37 | 1 | $10^{-2}$ | 1 | 1 |

[1]Efficiency of Plaquing determined on NCK203 derivative containing pTRK99 (Prf+), pTRK18 (Hsp+), pTRK323 (Per50), pTRK361 (Per31).

These results indicated that when bacteriophage ul36 infected *L. lactis* NCK203 with the abortive mechanism Prf, two distinct progeny phages were released: ul36 and ul37. Phage ul37 is a new Prf$^r$ recombinant phage and differs from ul36 in morphology, antibody reaction and genomic organization.

EXAMPLE 8

Location of ul37 Sequences in the NCK203 Chromosome

*L. lactis* NCK203 harbors one inducible prophage in its chromosome. Southern analysis revealed that this prophage is also a member of the P335 species (data not shown). Electron microscopic analysis showed that the prophage had similar head and tail dimensions to ul36 but had a different base plate (data not shown). The base plate contained 4 spikes and was strikingly different from ul37, suggesting that the inducible prophage harbored in NCK203 is not the progenitor of ul37.

Southern hybridization experiments were conducted between the DNAs of phages ul36, ul37, and the inducible prophage within the chromosome of NCK203 (data not shown). The replicating prophage DNA was visualized as amplified DNA bands coming through the background of NCK203 chromosomal DNA. It was seen that ul36 shared major DNA homology with ul37 and little homology to the prophage. Some homology was expected since all three phages belonged to the same phage species, namely P335. A weak signal obtained with the chromosome correlated to the lower concentration of the prophage DNA (one copy per genome). It was noteworthy that the DNA restriction fragments of ul37 that shared homology to ul36 were the same DNA fragments that shared homology with the phage P335 DNA (data not shown). These observations indicated that DNA acquired by phage ul37 did not originate from another P335 phage.

The data from the Southern hybridizations in combination with the electron micrographs indicated that ul37 is a recombinant phage bearing DNA fragments originating from both ul36 and the chromosome of NCK203, but not from the inducible prophage present in NCK203.

EXAMPLE 9

Disruption of NCK203 Chromosomal Sequences that Contribute to ul37

Figure 3:
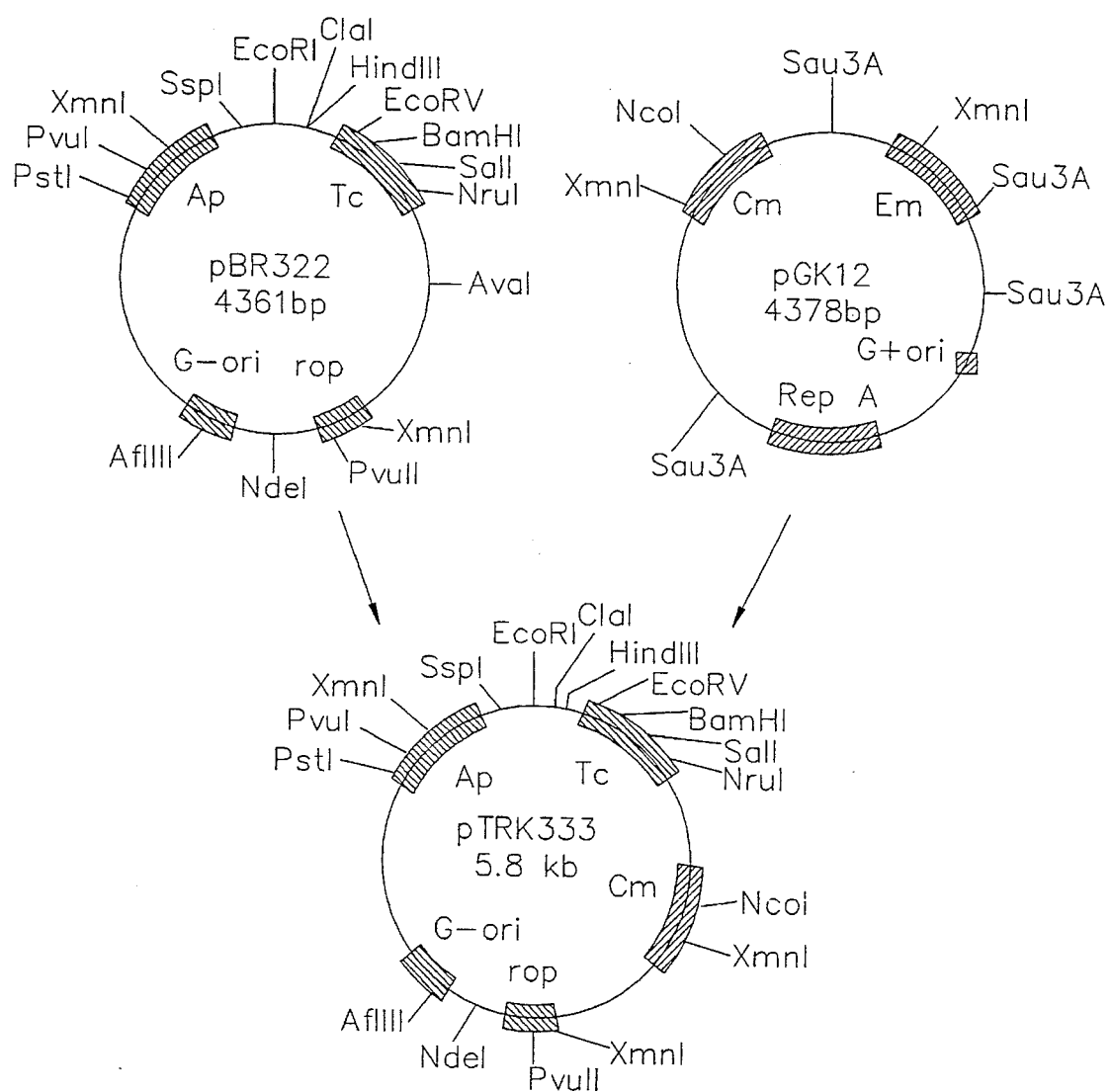
FIG. 3 is a schematic diagram of the construction of integration vector pTRK333.

To evaluate whether NCK203 chromosomal sequences contributed directly to the appearance of ul37, an integration strategy was employed. A gram-positive "suicide vector" (pTRK333), deficient in a gram-positive origin of replication was constructed using a pBR322 base replicon (Leenhouts et al., *Appl. Environ. Microbiol.*, 55:394(1989)) (FIG. 3 and Example 2, above). Phages ul36 and ul37 were digested with HindIII (data not shown) and the nine largest HindIII fragments from ul36 and the ten largest HindIII fragments from ul37 were individually gel purified and cloned into the unique HindIII site of pTRK333. Ligation mixtures were electroporated in *E. coli* DH5a and Ap$^r$ Tc$^s$ clones selected. Eight of the nine HindIII fragments from phage ul36 (pTRK334 to pTRK341, TABLE 2) and six of the 10 HindIII fragments from ul37 (pTRK342 to pTRK347, TABLE 2) were successfully cloned. These 14 clones were individually electroporated into *L. lactis* NCK203. Cm$^r$ transformants were obtained for only one of the eight plasmids (pTRK340) carrying DNA from phage ul36. Five of the six plasmids (pTRK342, pTRK343, pTRK344, pTRK345, pTRK347) containing ul37 DNA yielded transformants.

Plasmid analysis of representative transformants showed that no new plasmids were acquired (data not shown). No transformants were obtained with the vector pTRK333. Compared to the other plasmids, an unusually high number of integrants (up to $10^3$ cfu/mg of DNA) were obtained when pTRK343 was electroporated into *L. lactis* NCK203. The number of integrants for the other plasmids varied from 1 to 15 cfu/mg of DNA.

Site-specific integration was demonstrated by Southern blots of pulse-field gels for the transformants bearing inserts of pTRK340, pTRK343, pTRK344, pTRK345, and pTRK347 (data not shown). An analysis of six pTRK345 transformants was evaluated (data not shown). Homology was observed between the 1.55 kb HindIII fragment of ul37 cloned in pTRK345 and the chromosome of NCK203. pTRK345 integrated at the same site in six NCK203 transformants which were examined. Upon integration of pTRK345, the homologous fragment in NCK203 disappeared and a single junction fragment appeared. The Cm$^r$ gene used in this study is expressed at low levels in *L. lactis* and one gene copy is insufficient to confer Cm resistance (Leenhouts, et al., *Appl. Environ. Microbiol.*, 55:394(1989)). Therefore, similar to previous observations (Casey, et al., *Appl. Environ. Microbiol.*, 58:3283(1992); Leenhouts, et al. *Appl. Environ. Microbiol.*, 55:2568(1991)), amplification occurred upon selection with 5 μg/ml of chloramphenicol. A 7.4 kb fragment existed, representing amplified copies of pTRK345 integrated into the NCK203 chromosome. The amplified structure is likely to have obscured detection of a second junction fragment expected to result from pTRK345 integration.

Pulse field gel electrophoresis further confirmed integration of various pTRK333::ul37 recombinant plasmids into the chromosome of NCK203 (data not shown). The integration occurred at different position but within the same 230 kb ApaI fragment of the NCK203 chromosome. This band increased in size upon integration of the various plasmids. While the plasmids were approximately 7 to 8 kb, the increase in the band size was much larger due to amplification of the integrated structure. Integration of the various plasmids carrying DNA from phage ul37 indicated that some of the DNA fragments found in the ul37 genome originated from the NCK203 chromosome.

All the pTRK333::ul37 integrants were examined for their ability to propagate phages. Phages ul36 and ul37 propagated on the integrants to the same degree as on the parental strain NCK203 (data not show). The NCK203 prophage was also inducible from all integrants upon exposure to mitomicin C.

These results indicated that pTRK333::ul37 integration events did not occur within the prophage and confirmed that the DNA homology which exists between ul37 and the NCK203 chromosome is not related to the inducible prophage.

EXAMPLE 10

Disruption of ul37 Appearance

Plasmid pTRK99 (Prf$^+$, Em$^r$) was electroporated into NCK203 bearing pTRK333::ul37 integrants. Co-selection was made with chloramphenicol (5 μg/ml) and erythromycin (2 μg/ml) to select for Prf$^+$ transformants and maintain the pTRK333::ul37 integrants. When the Prf$^+$ integrants were challenged with phage ul36, the phage was restricted to an EOP of $10^{-3}$ and pinpoint plaques were observed. Larger plaques were also observed at an EOP of $10^{-5}$, but these were smaller (1 mm diameter) than those obtained with ul37 (2 mm). Characterization of phages purified from single small plaques again revealed a ul36 genotype, (same DNA restriction patterns) and phenotype ($Prf^s$ and $Per50^s$). Phage purified from single large plaques revealed a ul36 genotype but a $Prf^r$ $Per50^s$ phenotype; indicating that the $Prf^r$ phenotype did not result from a major genetic rearrangement. No phages similar to ul37 were isolated from any of the $Prf^+$ NCK203 integrants after infection with ul36.

These results indicated that disruption of resident NCK203 chromosome sequences by site-specific integration events eliminated the appearance of ul37 from $Prf^+$ NCK203 cells, and confirmed the absence of possible contaminating phage in the ul36 stocks that could give rise to ul37.

The foregoing examples are illustrative of the present invention, and are not to be construed as limiting thereof. The invention is defined by the following claims, with equivalents of the claims to be included therein.

That which is claimed is:

1. A method of identifying a bacterial DNA sequence capable of recombining with DNA of a predetermined bacteriophage, said method comprising:
   (a) introducing a bacteriophage defense mechanism into a bacterium of genera Lactococcus;
   (b) culturing said Lactococcus bacterium in the presence of a first lytic bacteriophage to produce a bacterial culture, said first lytic bacteriophage being sensitive to said bacteriophage defense mechanism wherein said first lytic bacteriophage is selected from the group consisting of P335, c2 and 936 bacteriophage;
   (c) isolating from said bacterial culture a second lytic bacteriophage which is resistant to said bacteriophage defense mechanism, said second lytic bacteriophage being derived from said first lytic bacteriophage;
   (d) identifying DNA sequences present in said second lytic bacteriophage which are not present in said first lytic bacteriophage; and then
   (e) identifying a bacterial DNA sequence which is homologous to a DNA sequence of said second lytic bacteriophage identified in step (d);
   wherein said identified bacterial DNA sequence is capable of recombination with DNA of said first lytic bacteriophage.

2. A method of producing a recombinant bacterium for use in producing fermentative culture medium resistant to the appearance of new bacteriophage, said method comprising:
   (a) introducing a bacteriophage defense mechanism into a bacterium of genera Lactococcus;
   (b) culturing said Lactococcus bacterium in the presence of a first lyric bacteriophage to produce a bacterial culture, said first lyric bacteriophage being sensitive to said bacteriophage defense mechanism wherein said first lytic bacteriophage is selected from the group consisting of P335, c2 and 936 bacteriophage;
   (c) isolating from said bacterial culture a second lyric bacteriophage which is resistant to said bacteriophage defense mechanism, said second lytic bacteriophage being derived from said first lyric bacteriophage;
   (d) identifying DNA sequences present in said second lyric bacteriophage which are not present in said first lyric bacteriophage; and then
   (e) identifying a bacterial DNA sequence which is homologous to a DNA sequence of said second lytic bacteriophage identified in step (d);
   wherein said identified bacterial DNA sequence is capable of recombination with DNA of said first lytic bacteriophage;
   (f) cloning said homologous DNA sequence into an integration vector capable of homologous recombination with said Lactococcus bacterium chromosomal DNA and incapable of replication in said Lactococcus bacterium;
   (g) inserting said integration vector into said Lactococcus bacterium; and
   (h) selecting a recombinant bacterium in which said recombinant bacterium has undergone homologous recombination with said integration vector, such that said identified bacterial sequences are disrupted in said recombinant bacterium.

3. The method of claim 1 or claim 2 wherein said first lyric bacteriophage is selected from P335 bacteriophage.

4. A method according to claim 2, wherein said identified bacterial sequences are disrupted by insertion of an intervening sequence therein.

5. A method according to claim 2, wherein said identified bacterial sequences are disrupted by deletion thereof.

6. A method according to claim 2, further comprising the step of culturing said recombinant bacterium to provide a fermentative culture medium resistant to the appearance of new bacteriophage strains.

* * * * *

UNITED STATES PATENT AND TRADEMARK OFFICE
CERTIFICATE OF CORRECTION

PATENT NO. : 5,580,725

Page 1 of 2

DATED : December 3, 1996

INVENTOR(S) : Klaenhammer et al.

It is certified that error appears in the above-indentified patent and that said Letters Patent is hereby corrected as shown below:

On the title page;
    [56], after "Durmez et al." insert --,--.
    [56], after "Sanders et al." insert --,--.
    [56], after "Fitzgerald et al." add --,--.
    [56], O'Sullivan et al., replace "Trans," with --trans,--.
    [56], Klaenhammer, replace "R-esistant" with --Resistant--.
    Col. 12, Table I, replace "Ap4" with --$Ap^r$--, all instances.
    Col. 12, Table I, under SOURCE, replace first "this study" with --1*--; replace "Pel31" with --Per31--.
    Col. 13, Table I cont'd, characteristic 031, replace "Per31r" with --Per31s--; under LEGEND, replace "S1" with --SI--.
    Col. 13, Table II, LEGEND, replace "Microbial" with --Microbiol--.
    Col. 21, line 37, replace "lyric" with --lytic--.
    Col. 21, line 38, replace "lyric" with --lytic--.
    Col. 22, line 4, replace "lyric" with --lytic--.
    Col. 22, line 5, replace "lyric" with --lytic--.
    Col. 22, line 10, replace "lyric" with --lytic--.
    Col. 22, line 13, replace "lyric" with --lytic--.
    Col. 22, line 15, replace "lyric" with --lytic--.

UNITED STATES PATENT AND TRADEMARK OFFICE
CERTIFICATE OF CORRECTION

PATENT NO. : 5,580,725

DATED : December 3, 1996

INVENTOR(S) : Klaenhammer et al.

It is certified that error appears in the above-indentified patent and that said Letters Patent is hereby corrected as shown below:

Col. 22, line 39, replace "lyric" with --lytic--.

Signed and Sealed this

Third Day of June, 1997

Attest:

BRUCE LEHMAN

Attesting Officer

Commissioner of Patents and Trademarks